United States Patent [19]

Simonazzi

[11] Patent Number: 4,674,547

[45] Date of Patent: Jun. 23, 1987

[54] CONTAINER FILLING APPARATUS WITH ADJUSTABLE PRESSURE SEALING MEANS

[76] Inventor: Andriano Simonazzi, St. Via Laspezia 241/A, 43016 Parma, Italy

[21] Appl. No.: 782,816

[22] Filed: Oct. 2, 1985

[30] Foreign Application Priority Data

Oct. 2, 1984 [IT] Italy ................... 3589 A/84

[51] Int. Cl.⁴ .................. B65B 65/02; B65B 3/00
[52] U.S. Cl. .................... 141/263; 141/250; 141/266; 141/181
[58] Field of Search .................. 141/250–254, 141/260, 258, 263, 266, 284, 301, 279, 129, 144–146, 148, 149, 181, 182, 147, 351, 352, 152

[56] References Cited

U.S. PATENT DOCUMENTS

| | | | |
|---|---|---|---|
| 1,438,483 | 12/1922 | Garrett | 141/181 |
| 3,205,920 | 9/1965 | Cozzoli et al. | 141/258 X |
| 3,461,923 | 8/1969 | Riesenberg | 141/140 |
| 3,559,702 | 2/1971 | Riesenberg | 141/128 |
| 3,831,644 | 8/1974 | Berg et al. | 141/82 |
| 3,857,424 | 12/1974 | Roberts | 141/275 |
| 3,926,229 | 12/1975 | Scholle | 141/392 X |
| 4,308,900 | 1/1982 | Vadas | 141/258 X |

Primary Examiner—Stephen Marcus
Assistant Examiner—Ernest G. Cusick
Attorney, Agent, or Firm—Sughrue, Mion, Zinn, Macpeak, and Seas

[57] ABSTRACT

The container filling device includes a first piston slidably mounted within a first cylinder for raising and lowering a nozzle into and out of operative engagement with a container to be filled. A sealing ring is mounted on the lower end of the first piston for sealing engagement with the rim of a container to be filled and a passage is provided for allowing gas pressure within the container to enter the bottom of the first cylinder to provide a pressure differential on the first piston depending upon the diameter of the container. A second piston is slidably mounted for vertical reciprocating movement within a second cylinder and is operatively connected to the first piston. First and second pneumatic pressure supplies are connected to the second cylinder above and below the second piston for regulating the pressure applied between the sealing ring on the first piston and the rim of a container being filled.

4 Claims, 4 Drawing Figures

CONTAINER FILLING APPARATUS WITH ADJUSTABLE PRESSURE SEALING MEANS

BACKGROUND OF THE INVENTION

The present invention is directed to a container filling apparatus of the rotary type adapted to support a plurality of containers on a rotating table beneath a rotatable dispensing device having a plurality of axially moveable dispensing nozzles having sealing means for engaging the lip of each container respectively and more specifically to a pressure control arrangement for regulating the pressure of the sealing means on the lip of each container.

Although rotatable container filling apparatus are generally old and well known in the art a problem exists in the filling of thin walled tube shaped containers which have a very delicate rim surrounding the filling opening in the container. In filling such containers it is extremely difficult to obtain a good seal between the dispensing nozzle and the rim of the container due to the delicate nature of the container and accordingly it is difficult to obtain high production speeds.

SUMMARY OF THE INVENTION

The present invention provides a new and improved container filling apparatus of the rotary type having a plurality of axially reciprocating filling nozzles adapted to cooperate with a plurality of thin walled containers wherein the apparatus is provided with means for optimizing the sealing force between the dispensing nozzle and the rim of the container to prevent damage to the container.

The present invention provides a new and improved container filling apparatus of the rotary type having a plurality of reciprocating filling nozzles engageable with a plurality of containers wherein external double acting pneumatic means are operatively connected to the axially moveable dispensing nozzle for regulating the initial pressure engagement between sealing means on the dispensing nozzle and the lip of the container being filled as well as compensating for pressure differentials acting on the axially reciprocating nozzle during the actual filling process.

The foregoing and other objects, features and advantages of the invention will be apparent from the following more particular description of a preferred embodiment of the invention as illustrated in the accompanying drawings.

DETAILED DESCRIPTION OF THE INVENTION

Figure 1:
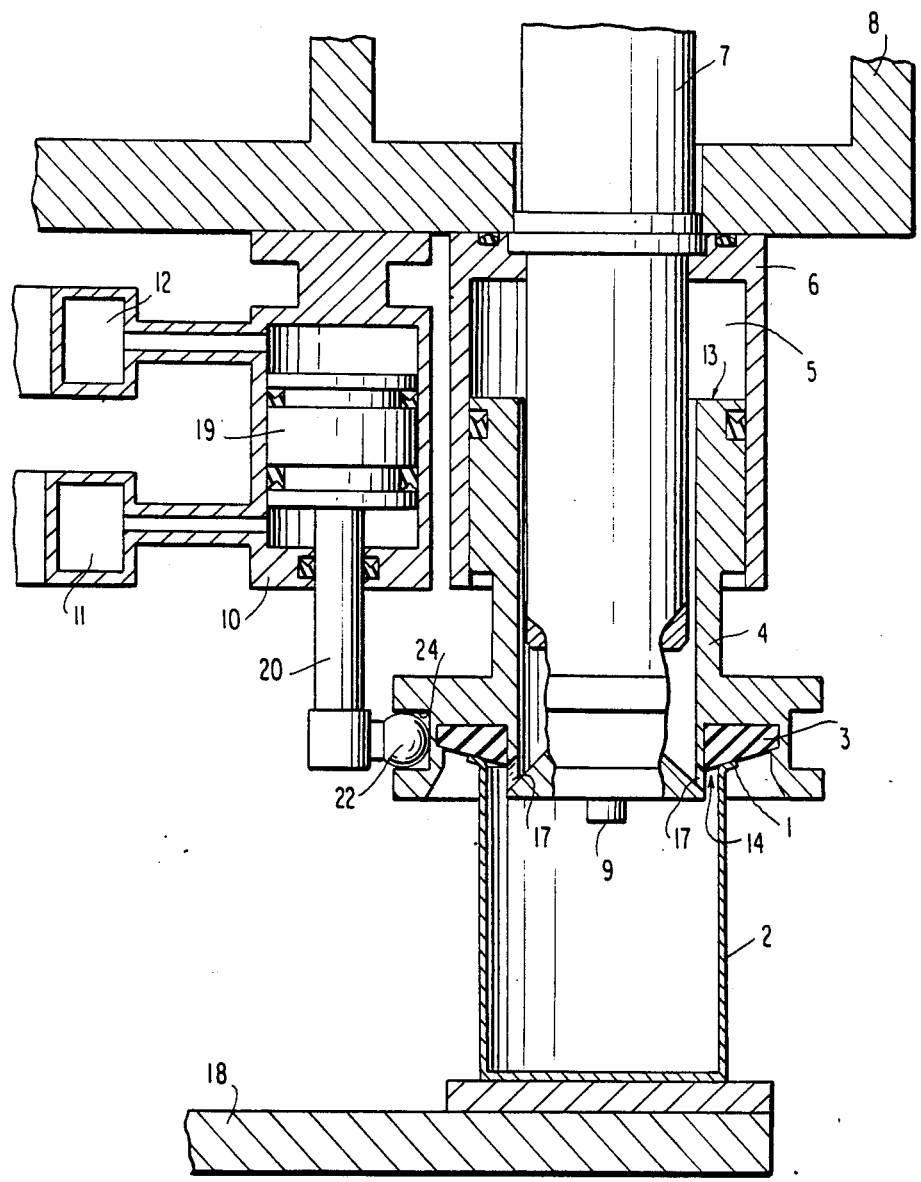
FIG. 1 is a side elevation view, partly in section, of a container, dispensing nozzle and pneumatic pressure means associated with the nozzle at a filling station of a continuous rotary filling apparatus.

The container filling apparatus according to the present invention is comprised of a rotatable table 18 adapted to support a plurality of containers 2. A reservoir, or reservoir means 8 is mounted for rotation with the table 18 and includes a pluality of dispensing devices 7 spaced about the periphery of the reservoir 8 with each dispensing device 7 being associated with a respective container 2. The remaining details of the rotary filling machine are old and well known and need not be described in detail. It is deemed sufficient for the purposes of the present invention to limit the discussion to a single filling station on the rotary filling machine.

A first cylinder 6 is sealingly connected to the underside of the reservoir 8 by any suitable means and an annular piston, or first piston 4 is slidably mounted within the chamber 5 of the cylinder 6 for vertical and reciprocating movement. A dispensing nozzle or nozzle means 9 is disposed within the annular piston 4 and is connected to the piston 4 for reciprocating movement therewith. An annular sealing member or sealing means 3 is located in an annular recess adjacent the bottom of the piston 4 and is adapted to sealingly engage the rim 1 of the container 2. A plurality of passages or passage means 17 are formed in the bottom of the nozzle 9 adjacent the sealing member 3 which communicate the interior of the container 2 with the telescopic chamber 5 in the cylinder 6.

Before starting the filling process the sealing member 3 has to be pressed with sufficient force against the rim 1 of the container 2 to guarantee a perfect seal which is essential for the initiation of the fluid flow through the nozzle 9 into the container 2. When the containers 2 are of the type having a relatively thin wall and a relatively delicate rim 1, the amount of pressure applied between the sealing member 3 and the rim 1 is generally quite small and must be accurately regulated in order to prevent damage to the rim 1 of the container 2. A pneumatic cylinder or second cylinder 10 is secured to the reservoir 8 adjacent the cylinder 6 and a second piston 19 is slidably mounted within the cylinder. A piston rod 20 which is integral with the piston 19 extends outwardly of the cylinder 10 and is provided with a ball type connector 22 which is disposed in an annular groove 24 in the end of the piston 4. First and second fluid pressure sources or pneumatic means 11 and 12 are connected to the cylinder 10 below and above the piston 19, respectively. The pressurized fluid may be air and the pneumatic pressure in each source may be regulated so as to accurately control the downward force applied by the sealing member 3 against the rim 1 of the container 2. Prior to the initiation of the actual filling operation the piston 19 is operated to provide sufficient pressure for obtaining a good seal between the sealing ring 3 and the rim 1 of the container 2. The value of the pressure ratio between the two sources 11 and 12 is also regulated during a filling operation to compensate for pressure differentials applied to the piston 4 as a result of the filling operation.

Figure 3:
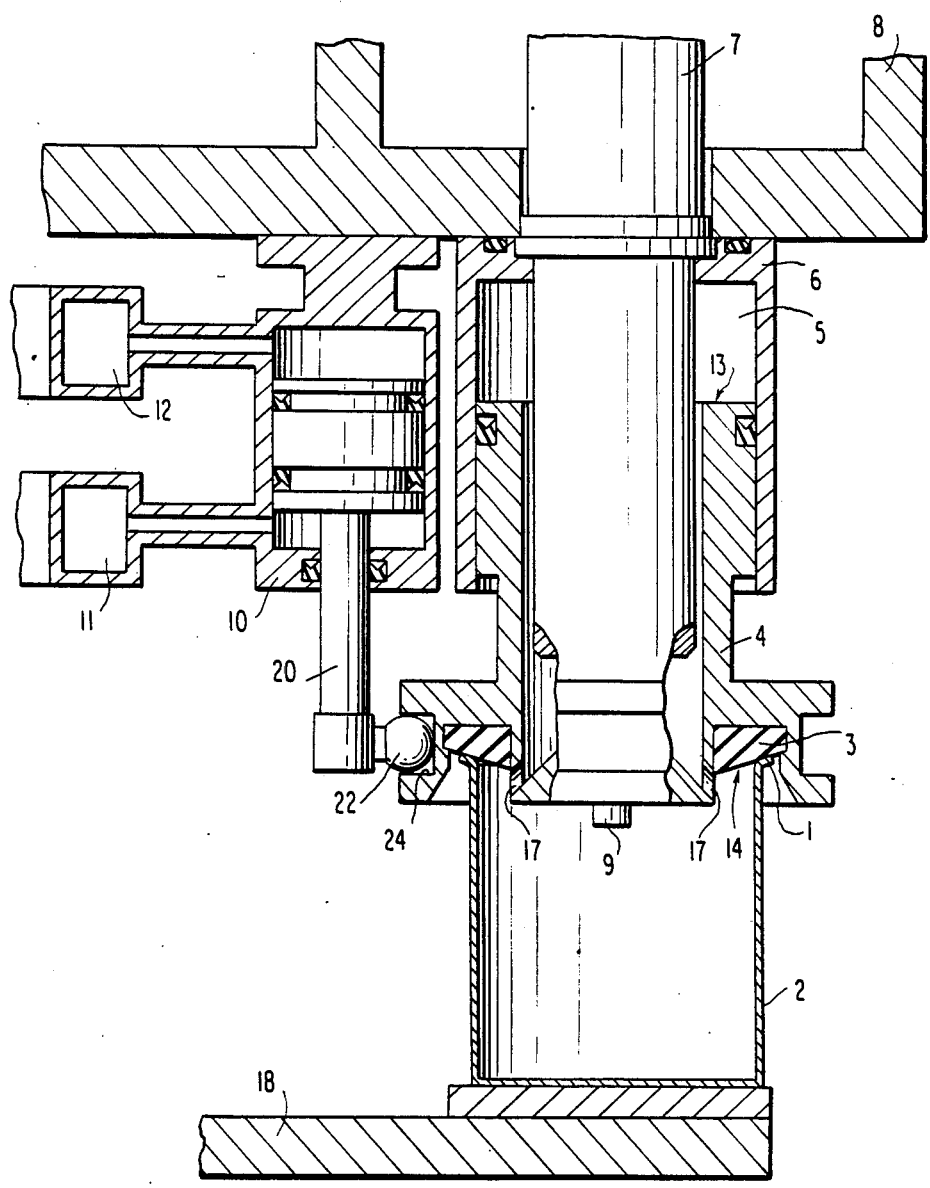
FIG. 3 is a view similar to FIG. 1 showing the filling nozzle in combination with a larger diameter container.
Figure 4:
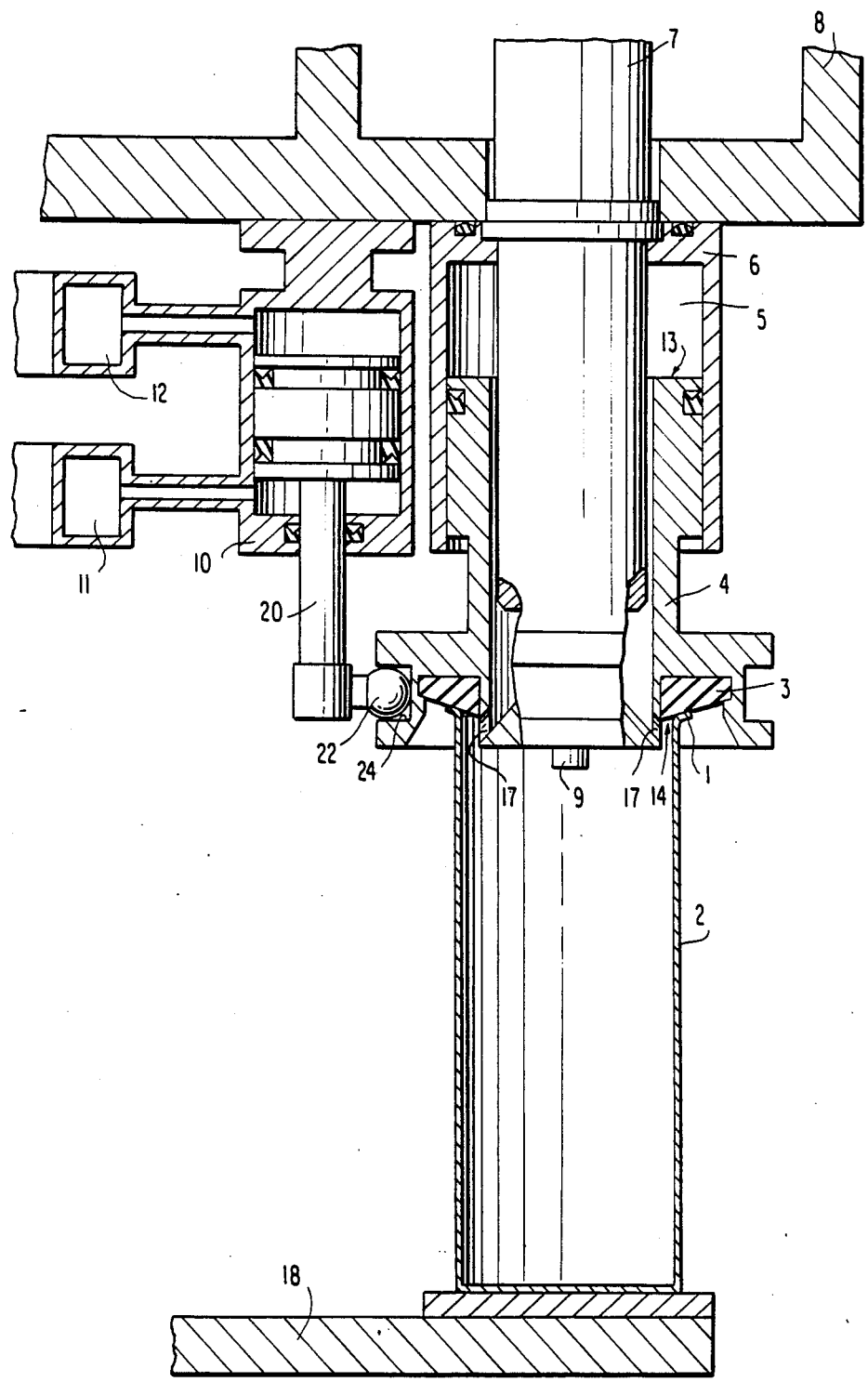
FIG. 4 is a view similar to FIG. 1 showing the filling nozzle in combination with a container having a greater axial length.

As the liquid to be filled is supplied into the container 2 through the nozzle 9 any gasses within the cylinder are forced upwardly through the passages 17 into the telescopic chamber 5. Thus the pressure in the chamber 5 will be exerted against the upper surface 13 of the piston 4 and the pressure within the container 2 will be exerted against the bottom of the nozzle 9 as well as that portion 14 of the sealing member 3 exposed to the interior of the container 2. Thus, while the active surface 13 is always constant, the active surface 14 on the sealing members 3 varies depending upon the diameter of the container being filled. As shown in FIG. 1 a relatively small diameter container is being filled while in FIG. 3 a relatively large diameter container is being filled. Thus the pressure differential acting on the piston 4 will vary depending upon the diameter of the container being filled. In order to optimize the sealing force between the sealing member 3 and the rim 1 of the container 2 the ratio of the pneumatic pressures in the source 11 and 12 an be adjusted depending upon the diameter of the containers being filled. The pneumatic pressure means for regulating the sealing pressure of the dispensing nozzle as described with respect to FIG. 1 is also equally effective for filling thin walled containers having a greater axial length as shown in FIG. 4.

Figure 2:
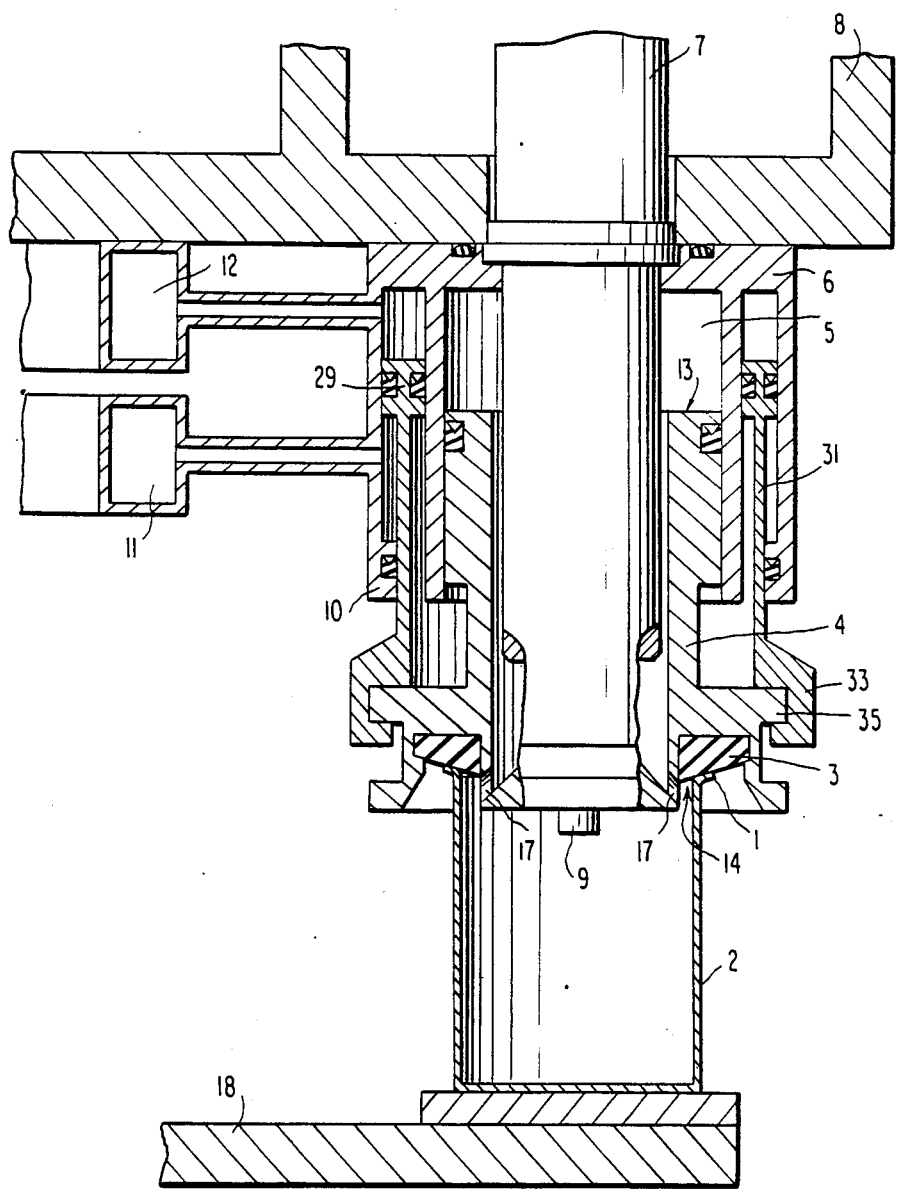
FIG. 2 is a sectional view similar to FIG. 1 showing a modified form of the pneumatic means associated with the dispensing nozzle.

In the embodiment of FIG. 2 the basic operation of the pneumatic pressure means is substantially the same as that described above with respect to the embodiment of FIG. 1. However the piston 29 which is operated by the pneumatic pressures from the sources 11 and 12 is concentrically disposed about the cylinder 6 for reciprocating movement relative thereto. A sleeve 31 extends downwardly from the piston 29 and terminates in a C-shaped bracket 33 which cooperates with a flange 35 on the lower end of the piston 4. Thus upon regulating the ratio of the pressures in the sources 11 and 12 the applied force between sealing member 3 and the rim 1 of the container 2 can be very accurately regulated both prior to the filling operation and during the filling operation depending upon the diameter of the container being filled.

While the invention has been particularly shown and described with reference to preferred embodiments thereof it will be understood by those in the art that the foregoing and other changes in form and details may be made therein without departing from the spirit and scope of the invention.

What is claimed is:

1. A container filling device comprising a table supporting a container at a filling station, reservoir means disposed above said table, nozzle means movably associated with said reservoir means for filling said container, a first cylinder surrounding said nozzle means and sealingly supported by said reservoir means, a piston mounted for reciprocating movement within said cylinder and connected to said nozzle means for raising and lowering said nozzle means, sealing means mounted on the lower end of said piston for engagement with a rim on said container, a passage means between said nozzle means and said piston for communicating the interior of the container being filled with the interior of said cylinder above said piston and pneumatic means operatively connected to said piston for regulating an applied force between said sealing means and the rim of a container being filled.

2. A container filling device as set forth in claim 1 wherein said pneumatic means comprises a second cyclinder mounted in close approximation to said first cyclinder, a second piston mounted for vertical reciprocating movement within said second cylinder and connected to said first piston and first and second fluid pressure sources comprising said pneumatic means and connected to said second cyclinder above and below said second piston for regulating the pressure engagement between said sealing means and the rim of the container being filled.

3. A container filling device as set forth in claim 2 wherein said second cylinder is disposed adjacent said first cylinder in spaced parallel relation thereto.

4. A container filling device as set forth in claim 2 wherein said second cylinder is disposed outwardly of and concentric to said first cylinder.

* * * * *